United States Patent [19]

Parent et al.

[11] 4,258,721

[45] Mar. 31, 1981

[54] SELF-CONTAINED PORTABLE HYSTEROSCOPE

[76] Inventors: Bernard Parent, 5, rue Paul Valéry, 75016 - Paris, France; Herbert Guedj, 362, rue Lecourbe, 75015 - Paris, France

[21] Appl. No.: 3,972

[22] Filed: Jan. 16, 1979

[30] Foreign Application Priority Data

Jan. 26, 1978 [FR] France .............................. 78 02177

[51] Int. Cl.³ .................... A61B 1/30; A61B 10/00
[52] U.S. Cl. .................................. 128/747; 128/6; 128/207.28
[58] Field of Search ............. 128/747, 207.26, 207.27, 128/207.28, 6–9

[56] References Cited

U.S. PATENT DOCUMENTS

| 2,544,931 | 3/1951 | Marco | 128/747 |
| 2,623,519 | 12/1952 | Cohen | 128/207.28 |
| 2,691,370 | 10/1954 | Wallace | 128/6 |
| 2,911,968 | 11/1959 | Schueler et al. | 128/6 |
| 4,061,135 | 12/1977 | Widran et al. | 128/6 |
| 4,106,493 | 8/1978 | Proctor | 128/747 |
| 4,175,545 | 11/1979 | Termanini | 128/6 |

OTHER PUBLICATIONS

"Gas Test Tube for Patency" (1940) pp. 326-332.

*Primary Examiner*—Kyle L. Howell
*Attorney, Agent, or Firm*—Fisher, Christen & Sabol

[57] ABSTRACT

The present invention relates to a hysteroscope of the type comprising an outer envelope forming a cannula, means for insufflation of a fluid, particularly a gaseous fluid, such as for example carbon dioxide, inside the uterine cavity to distend the walls thereof, and an inner envelope forming an endoscope tube, of smaller diameter than the outer envelope and adapted to slide therein, this inner envelope containing light transmission means for conducting light to the distal end of said inner envelope and comprising on the one hand means for mechanically placing the hysteroscope in operating position, substantially fluid-tight at the level of the cervix of the uterus and on the other hand a portable device for supplying said fluid, fast with said hysteroscope.

10 Claims, 9 Drawing Figures

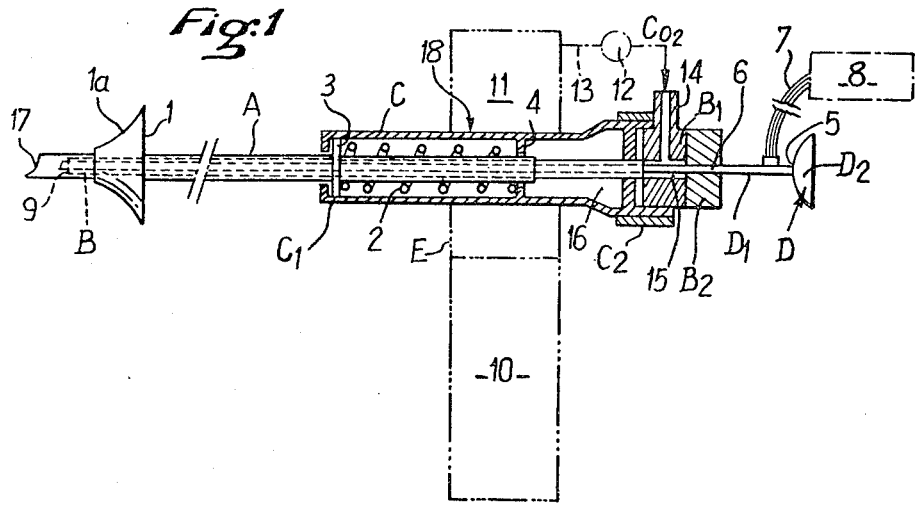
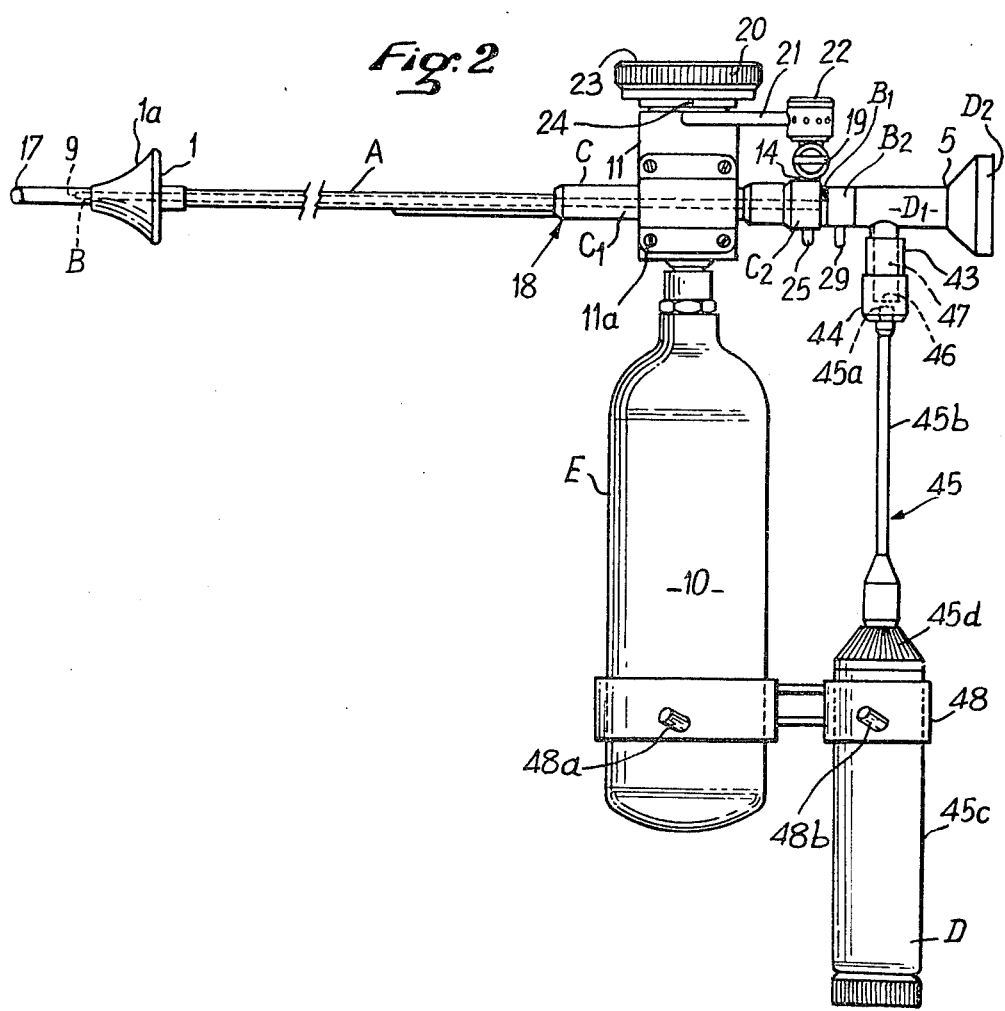

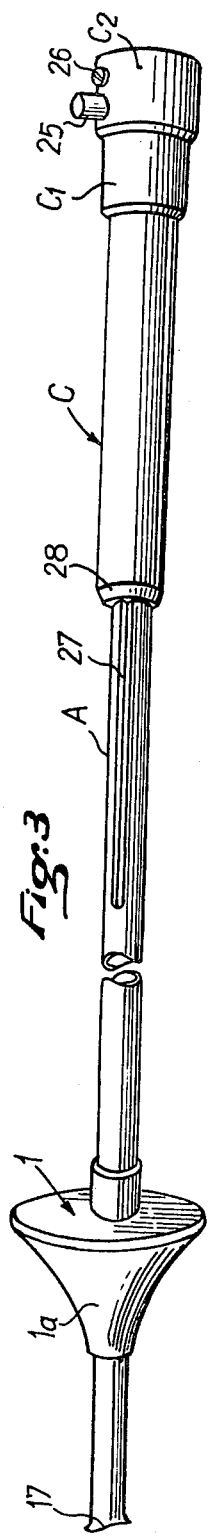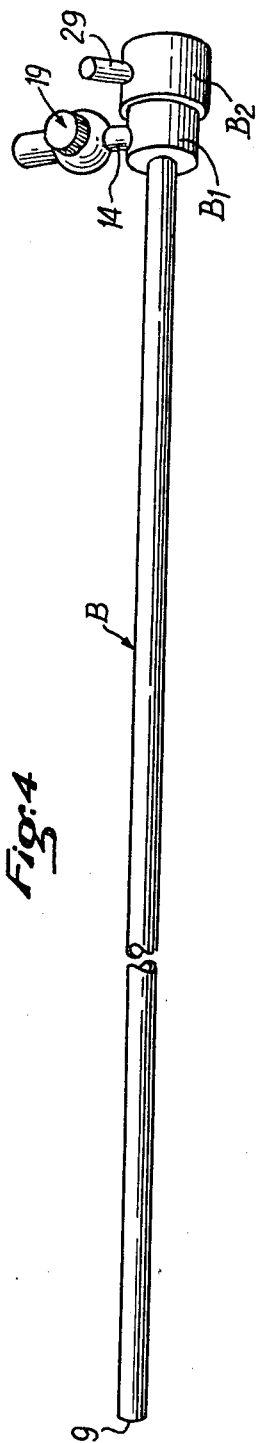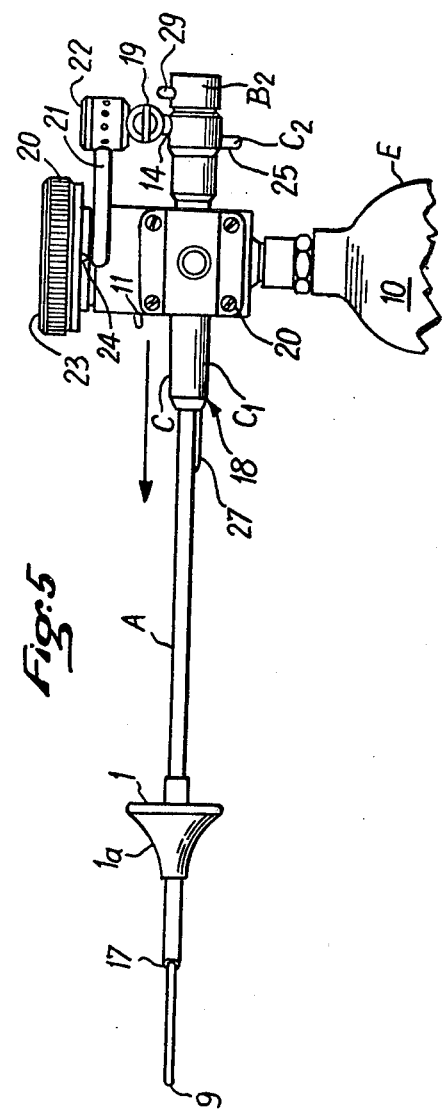

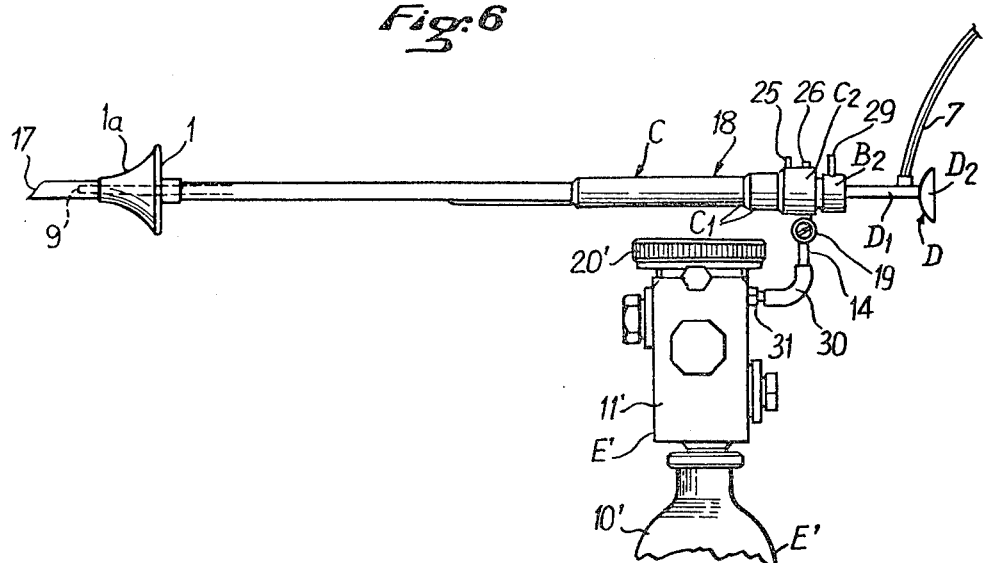
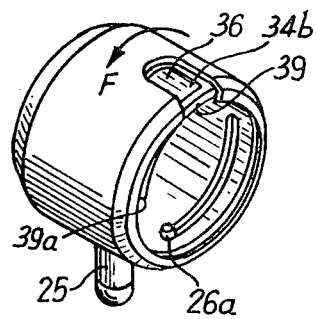
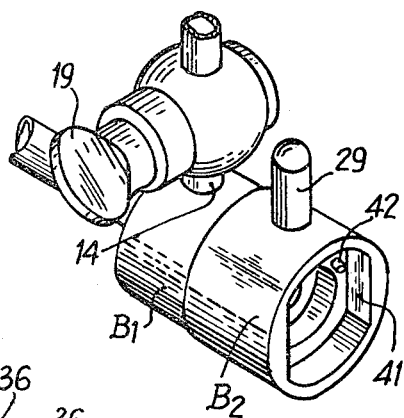
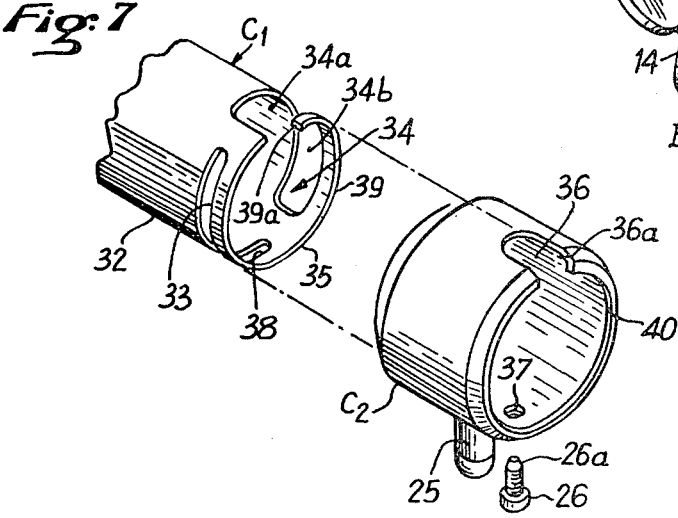

SELF-CONTAINED PORTABLE HYSTEROSCOPE

The present invention relates to a hysteroscope for diagnosis or observation, allowing an endoscopic examination of the uterus.

Hysteroscopes employing a gaseous fluid (incorrectly called "air" hysteroscopes) are already known, employing carbon dioxide for distending the uterine walls.

These apparatus provoke the distension of the uterus by a continuous insufflation of carbon dioxide under controlled pressure, lower than about 150 millibars. The release of carbon dioxide is effected at the level of the proximal part (or outer part) of the cervical canal, this expanding the narrow cervico-isthmic channel before any penetration and allowing an introduction without provoking any traumatism.

A cervical seal must then be effected, this being obtained by pneumatic gripping of the cervix, by means of a cannula provided with a suction disc applied and centered on the cervical orifice, this cannula being connected to a source of aspiration (vacuum of the order of 300 to 400 mm Hg); this cervical aspiration is exerted during the whole examination or operation.

The tube of the endoscope is introduced in the cannula in which it slides only after the gripping of the cervix by the suction disc of the cannula and this tube is firstly inserted only up to the level of the cervical orifice, after which the insufflation of the carbon dioxide begins; when the distension of the uterus is obtained, the tube of the endoscope may then advance in the cervico-isthmic channel, then into the uterine cavity.

Observation is effected with the aid of optical viewing means placed at the proximal end (or outer end) of the tube of the endoscope, the illumination being effected by a source of cold light connected to the tube of the endoscope, in the vicinity of the proximal end thereof, by a bundle of glass fibres which extends inside this tube, in a suitable sheath, up to the distal end (or inner end) of said tube.

Such apparatus present the essential advantage of giving a panoramic view of the uterine cavity.

However, the technique of panoramic vision with the aid of conventional "air" hysteroscopes presents numerous drawbacks:

complexity of the apparatus which must be connected to several outside sources by suitable pipes or cables: source of $CO_2$ ($CO_2$ cylinder under pressure with pressure reducing valve), source of vacuum, source of cold light;

undesirable continuous noise caused by the electric motor required by the source of vacuum;

numerous and delicate manipulations involving adjustments and monitoring (of flow or pressure), necessitating the presence of an assistant in addition to the practitioner.

risks of leakage at the pipe connections;

long duration of the examination (an hour to an hour and a half, with the result that the examination usually takes place only in an operating theatre);

relatively high percentage of failures due to the accumulation of these difficulties; and high cost of the equipment and examinations.

It is an object of the present invention to remedy these drawbacks.

The apparatus according to the invention may be used by the practitioner alone, without assistance; the examination lasts a short time (only 15 minutes) and may be carried out in the practitioner's consulting room; the apparatus is easy to handle; in particular, its cost price is much lower than that of a conventional "air" hysteroscope.

The hysteroscope according to the present invention, of the above-mentioned gaseous fluid type, is essentially characterised in that it comprises on the one hand means for mechanically placing the hysteroscope in operating position, substantially fluid-tight at the level of the cervix of the uterus and on the other hand a portable device for supplying said fluid, integrally combined with said hysteroscope.

In other words, the present "air" hysteroscope according to the present invention is completely self-contained and it grips the cervix of the uterus solely by mechanical means, without employing pneumatic means proceeding by aspiration.

The source of light is advantageously supplied by at least one electric battery integrally combined with said hysteroscope.

The invention will be more readily understood on reading the following description with reference to the accompanying drawings, in which:

FIG. 1 shows a diagram, partly in axial section and partly seen from outside, of the hysteroscope of the present invention.

FIG. 2 shows an outside view, in elevation, of a hysteroscope according to the preferred embodiment of the present invention.

FIG. 3 shows a view in perspective of the outer envelope of the hysteroscope of FIG. 2, provided with its element for abutment on the cervix of the uterus and of the sleeve, with its cooperating elements, of the sliding assembly;

FIG. 4 shows a view in perspective of the inner envelope, with its cooperating elements, of the hysteroscope of FIG. 2;

FIG. 5 shows a view in elevation of the hysteroscope of FIG. 2, but in an advanced position of the sliding assembly with respect to the outer envelope, the position illustrated corresponding to the state of maximum advance of the sliding assembly during an endoscope examination;

FIG. 6 shows an outside view of a hysteroscope according to another embodiment of the invention;

FIG. 7 shows an exploded view of the means for locking the proximal end of the sleeve of the sliding assembly of the hysteroscope of FIG. 2;

FIG. 8 shows a view in perspective of these locking means, in the locking position.

FIG. 9 shows a view in perspective of the proximal end of the inner envelope of the hysteroscope of FIG. 2 and means for locking said latter with respect to the optical viewing device.

Referring now to the drawings, the hysteroscope shown schematically in FIG. 1 comprises the following parts:

an outer envelope A of cylindrical form, forming cannula, this outer envelope being combined with an element 1 having a front face 1a for abutment on the cervix of the uterus;

a tubular sleeve C comprising a tubular body $C_1$ and a locking ring $C_2$, this sleeve being permanently coupled to the outer envelope A, with the interposition of a helical spring or other elastic means 2 between a flange 3 of the outer envelope and a part of the sleeve C, such as a shoulder 4 of said tubular body;

an inner envelope B, forming an endoscope tube, of smaller outer diameter than the inner diameter of the outer envelope A and consequently slidable inside said latter, this inner envelope B being fast with a locking member $B_1$ and a locking connection ring $B_2$; this locking member $B_1$ being adapted to cooperate with the locking ring $C_2$ of the sleeve C, so that the inner sleeve B is made attached to the sleeve C;

an optical viewing device D comprising an eyepiece $D_2$ and a tube $D_1$ whose proximal end 5 is attached to said eyepiece and whose distal end is located at the level of the distal end of the inner envelope; a part 6 of this tube being adapted to be locked, as shown, in the locking connection ring $B_2$ of the inner envelope B, so that the inner envelope B and the tube $D_2$ are connected with each other; this optical viewing device D is connected, via a glass fibre cable 7, to the outside source of light 8 which is preferably a source of cold light; the glass fibre cable 7 extends to the inside of the hysteroscope, taking the passage determined by the tube $D_2$, this extension terminating at the distal end 9 of the inner envelope B; according to a variant, all or part of the cable 7 and its extension may be replaced by a tube of silica, glass or quartz or any other means and/or substances ensuring the transmission or conduction of light;

a device for supplying fluid for the distension of the uterine wall, particularly a device supplying carbon dioxide, denoted by reference E, which comprises a container 10 containing compressed carbon dioxide in the liquefied state, a support 11 for this container, which support is preferably removably fixed on the sleeve C, and a pressure reducing valve 12 for connecting the compressed carbon dioxide with the pipe 13 connected to the inlet terminal 14 of the locking member $B_1$ which communicates with the inner space of the inner envelope so that the carbon dioxide may be supplied to the distal end 9 of this envelope.

This hysteroscope may be held by one operator only, by using the container 10 as a handle.

For an examination, the sleeve C, the inner envelope B and the optical viewing device D are joined together, as shown in FIG. 1, so that these elements form a sliding assembly 18 which is adapted to slide with respect to the outer envelope A and to the abutment element 1, this relative movement involving the compression (from the state shown in FIG. 1) or the decompression of the spring 2; this relative movement being effected, after abutment of the face 1a of the abutment element 1 with the cervix of the uterus, by forward movement of said sliding assembly 18, this movement being applied by the operator with one hand, holding the container 10 forming a handle.

This sliding movement has for its effect, preferably in conjunction with a pulling force exerted on a gripping tool, as indicated hereinabove, to strongly apply the abutment element 1 hermetically against the cervix of the uterus, to cause the distal end 9 of the inner envelope B to leave the outer envelope A and to introduce this distal end 9 into the uterus; the distal portion of the outer envelope A, i.e. the portion thereof which extends between its distal end 17 and the abutment face 1a of the abutment element 1, being substantially equal to the length of the narrow cervico-isthmic channel.

The advance of the distal end 9 of the inner envelope B beyond the distal end 17 of the outer envelope A takes place only after distension of the uterine wall by insufflation of carbon dioxide, which is maintained, as in the conventional hysteroscope for the whole duration of the examination.

The distal portion of the outer envelope A could, according to a variant, be shorter than the length of the narrow cervico-isthmic passage so that the wall thereof may be observed without the vision being hindered by said distal portion.

Of course, for the whole duration of this examination, the thrust on the handle 10 must be maintained, so as to maintain not only a permanent contact, but also a permanent fluid tightness at the level of the cervix of the uterus, due to the contact, with pressure, of said abutment element 1.

When the examination is terminated, it suffices to release the thrust on the handle forming container 10, to return the above-mentioned sliding assembly 18 into rear position, this being facilitated by the action of the spring 2 functioning as means for elastically returning the sliding assembly 18 into its rear or rest position; from this position, it suffices to displace the sliding assembly further to the rear to extract the outer tube 1, forming cannula, and its abutment element 1, from the vaginal cavity.

FIG. 2 shows a hysteroscope according to the preferred embodiment of the invention, the same constituent elements as in the schematic view of FIG. 1 being designated by the same reference figures or letters. The apparatus is in the rest position of the sliding assembly 18, the inner envelope B being in position retracted inside the outer envelope 1. It will be noted that the inner envelope B, its locking member $B_1$ and its locking connection ring $B_2$ are shown in the position where they are already connected to the sleeve C, due to the reciprocal locking of the sleeve C and the locking ring $B_1$ attached to the inner envelope B.

This Figure shows that the device for supplying carbon dioxide comprises a small cylinder 10 for liquefied $CO_2$ under pressure, which may for example be made of a light alloy, the support 11 being attached to the tubular body $C_1$ of the sleeve C by means of four screws such as 11a. The knurled knob 20 controls a means of regulating the flow of carbon dioxide, placed downstream of a pressure reducing valve incorporated in the support 11, a conduit 21 for circulation of the carbon dioxide, a safety valve 22 and a stop cock 19; the adjusting knob 20 enables the flow of carbon dioxide to be regulated for example to values ranging from 15 to 150 cm$^3$/min, a graduated scale 23 moving opposite an index 24 allowing the flow to be indicated; the safety valve 22 is for example regulated so as to prevent the pressure of carbon dioxide from reaching the limiting value of 150±10 millibars.

The weight of this hysteroscope is for example of the order of 1 kg, distributed as follows: empty carbon dioxide cylinder: 0,300 kg; charge of carbon dioxide: 0,150 kg; support with flow adjusting device, safety valve and means for fixing the support on the sleeve: 0,450 kg; inner envelope, outer envelope and sleeve with their appendices up to the locking connection ring $B_2$: 0,100 kg.

It is seen that the optical viewing device D comprises, in addition to the tube $D_1$ and the optical viewing means $D_2$, a terminal 43 attached to the tube $D_1$ containing the light sensitive area located at one end of the bundle of glass fibre. A removable connection ring 44 and the source of light 45 comprises the incandescent lamp 45a, the tube 45b containing the electrical conductors connecting this lamp to electric batteries and the sleeve 45c forming a casing for said batteries, for example two cylindrical batteries of 1,5 volts. The circuit supplying the lamp 45a also comprises a rheostat actuated by the knurled knob 45d for adjusting the light intensity; it is seen that the lamp 45a is located virtually in contact with the extreme plane 46 of section of the bundle of optical fibres 47 when the source of light 45 is connected to the terminal 43 via the connecting ring 44. A two-ring band 48, joins the $CO_2$ supply device E and the source of light 45 and increases the rigidity of the whole hysteroscope without hindering gripping of the cylinder 10 forming a handle and manipulation thereof, this band 48 being tightened on these elements by screws 48a and 48b with milled heads.

In FIG. 3, only that part of the hysteroscope has been shown which is formed by the coupling of the outer envelope A, provided with its abutment element 1, and of the sleeve C constituted by the tubular body $C_1$ and the locking ring $C_2$ on which projects a stud 25 and the head of a screw 26 whose roles will be explained with reference to FIGS. 7 and 8. It will be noted that the movement of translation of the sleeve C with respect to the outer envelope A is guided by a longitudinal bead 27 forming a guide rail, which cooperates with a notch (not shown) in the transverse wall located at the level of the distal end 28 of the sleeve C, this bead preventing any relative rotation between the outer envelope A and the sleeve C (or the sliding assembly 18).

FIG. 4 shows the inner envelope B with its attachments constituted by the locking member $B_1$ and the locking connection ring $B_2$; it will be noted that the locking member $B_1$ has an outer diameter allowing the introduction of this member inside the locking ring $C_2$ of the sleeve C; this Figure shows that the carbon dioxide inlet terminal 14 carries the stop cock 19.

A notch in the outer peripheral edge of the locking ring $C_2$ (not visible in FIG. 3, but visible in FIGS. 7 and 8), allows passage of the base of the terminal 14 when the locking member $B_1$ is locked on the locking ring $C_2$; FIG. 4 also shows that the locking connection ring $B_2$ comprises a manoeuvring stop 29 facilitating the connecting manoeuvre, with locking, of the inner envelope B, via said locking ring $B_2$, with the proximal end of the tube of the optical viewing device D (not shown in FIGS. 2 to 4, but shown schematically in FIG. 1, which device is of a structure known per se).

FIG. 5, which illustrates the maximum position of advance of the sliding assembly 18 with respect to the outer envelope 1, shows that the distal end 9 of the inner envelope B projects beyond the distal end 17 of the outer envelope A, by a length for example of the order of 42 mm; this position corresponds to the maximum compression of the spring 2 (FIG. A) and is obtained when, the abutment element 1 having been applied against the cervix of the uterus, the sliding assembly has been pushed to a maximum in the direction of the uterus; stops (not shown in the Figures) enable the maximum degree of advance of the mobile assembly 18 with respect to the outer envelope A to be defined with the greatest possible accuracy.

The hysteroscope according to the embodiment of FIG. 6 is distinguished from that of FIGS. 2 to 5 in that the $CO_2$ supply device E' is not fixed, via the support 11', on the envelope C, the connection between this device and the sliding assembly 18 being solely ensured by the pipe 30 which is connected on the one hand to the $CO_2$ outlet terminal 31 connected to said device and on the other hand to the $CO_2$ inlet terminal 14 carrying the stop cock 19, which is attached to the locking member $B_1$ of the inner envelope B. The pipe 30 may in particular be short and rigid, as shown, or supple and of any suitable length.

FIG. 7 shows that the tubular body $C_1$ of the sleeve C terminates, on the locking ring $C_2$ side, in an end part 32 which is embedded in the locking ring $C_2$ which is movable in rotation with respect to said end part 32 which is fixed; this end part 32 comprises an arcuate groove 33 which passes through its wall and a recess 34 terminating in a notch 34a in the peripheral edge 35 of said end part 32 and by a transverse clearance 34b extending the notch 34a. The locking ring $C_2$ comprises a notch 36 superposable on the notch 34a of the end part 32; in addition, the locking ring $C_2$ comprises a tapped conduit 37 which passes through its wall and which cooperates with the screw 26 of which the end 26a projects, when the hysteroscope is in operating position, inside said locking ring $C_2$, said end 26a being engaged in the groove 33 of the end part 32 when the hysteroscope is mounted. It will be noted that, when the notches 34a and 36 are superposed, the end of the screw 26 is then located, in the groove 33, in the position shown in mixtilinear lines at 38, at one of the ends of said groove (right-hand end with respect to the user); in this relative position of the end part 32 and the locking ring $C_2$, the end 39a of the tongue 39 determined between the transverse clearance 34b and the peripheral edge 35 is substantially in line with one of the longitudinal edges 36a of the notch 36; this relative position of the tubular body $C_1$ and of the locking ring $C_2$ allows the introduction of the locking member $B_1$ inside the assembly formed by the end part 32 and the locking ring $C_2$, the terminal 14 then being engaged in the superposed notches 34a and 36, without being hindered by the tongue 39a; it will be noted that only this relative position of the tubular body $C_1$ and of the locking ring $C_2$ allows the introduction of the locking member $B_1$, carried by the inner envelope B, in the sleeve C. The end part 32 comprises an inner transverse wall (not visible in FIG. 7, but shown in FIG. 1) against which the locking member $B_1$ abuts when the terminal 14 is introduced to the bottom of the notches 34a and 36, a seal (not shown in FIGS. 7 and 8), attached to said transverse wall, being interposed between the latter and the locking member $B_1$; of course, as may be seen in FIG. 1, this transverse wall comprises a central opening for the passage, with clearance, of the inner envelope B.

FIG. 8 shows the relative positions of the tubular body $C_1$ and of the locking ring $C_2$ in the position of locking of the locking member $B_1$ in the sleeve C; however, to render the drawing more clear, FIG. 8 does not show the locking member $B_1$; in this position ring $C_1$ has been rotated counterclockwise approximately 170° so that the end 26a of the screw 26 is at the opposite end of the groove 33, with respect to the position occupied in FIG. 7, while the notch 36 of the locking ring $C_2$ is superposed on the bottom of the transverse clearance 34b of the groove 34 of the end part 32, the tongue 39 then being placed opposite the notch 36 so as to prevent the extraction of the terminal 14 engaged in said notch 36 and the bottom of the clearance 34b. It is therefore seen that, in this position, the inner envelope B, carrying the locking member $B_1$ and the locking connection ring $B_2$ is locked in the sleeve C; the elasticity of the tongue 39, abutting against the inner face of the peripheral edge 40 of the locking ring $C_2$ prevents any spontaneous rotation of the locking ring C₂ with respect to the sleeve C.

Unlocking is effected by manually controlled rotation of the locking ring C₂ in the direction of arrow F until the end 39a of the tongue 39 returns into line with the edge 36a of the notch 36, thus allowing the extraction of the sleeve 14 and consequently of the inner envelope and its elements B₁ and B₂; the catch 25 facilitates this rotation.

FIG. 9 shows the same elements as in FIG. 4; in addition, the structure of the end of the locking connection ring B₂ is seen, adapted to cooperate with the zone 6 of the tube of the optical viewing device D (cf. FIG. 1); this adaptation is effected by the introduction of said tube, in a suitable orientation with respect to the ring B₂, and rotation, so that catches connected to zone 6 are housed beneath flat portions such as 41, against which they abut by elastic means 42.

We claim:

1. A self-contained portable hysteroscope comprising, in combination:
   a pair of elongated hollow relatively axially slidable elements to be inserted into the uterine cavity comprising a cannula defining an outer envelope, and an endoscope tube of smaller diameter than the cannula and axially slidably received therein;
   handle means attached to at least one of said pair of elements to be grasped by one hand for manipulating said hysteroscope;
   means attached to at least one of said pair of elements to support a self-contained source of gas and a self-contained source of light;
   said endoscope tube including optical viewing means for conducting light from said light source to the distal end of the endoscope tube and to return an image of the area illuminated to the proximal end of the tube;
   conduit means for conducting gas from said source to the distal end of said endoscope tube for detending the walls of the uterine cavity;
   said outer envelope being provided with means at the distal end for establishing and automatically maintaining a fluid-tight seal with the entrance to the cervix of the uterus when manipulated by said handle by one hand.

2. A hysteroscope as defined in claim 1, wherein said source of light includes an electrical battery for said light source.

3. A hysteroscope as defined in claim 1, wherein said outer envelope includes an abutment means for said fluid tight seal, the forward surface of the abutment means being defined by a surface of revolution of tapering cross-section as it approaches the distal end, the distal end of the envelope projecting beyond said abutment means a distance substantially equal to the length of the narrow cervico-isthmic channel.

4. A hysteroscope as defined in claim 1, wherein the proximal end of said endoscope tube includes a sleeve surrounding and extending along a portion of the proximal end of the outer envelope, and elastic means within said sleeve connected with the outer envelope to urge the inner envelope in a rearward direction to retract the inner envelope within the outer envelope and to permit the inner envelope to be forwardly projected by force exerted on said handle means when the abutment means is in contact with the cervix.

5. A hysteroscope as defined in claim 4, wherein said means to support a source of gas comprises container means removably connected to said sleeve for containing a supply of liquefied gas, and said conduit means includes a pressure-reducing valve.

6. A hysteroscope as defined in claim 4, wherein said source of light is connected to said inner envelope and comprises an incandescent lamp, and an electric battery for said lamp, and said optical viewing means comprises a bundle of optical fibers.

7. A hysteroscope as defined in claim 4, wherein said inner envelope is provided with a locking member, and said sleeve comprises a tubular body removably mounted on the inner envelope by detachable connection with said locking member.

8. A hysteroscope as defined in claim 7, wherein said tubular member includes sealing means for confining gas to said endoscope tube when in locked position.

9. A hysteroscope as defined in either one of claims 5 or 7, wherein said locking member is provided with a passage forming a portion of the conduit means for conducting gas to said inner envelope.

10. A hysteroscope as defined in claim 4, wherein said means for conducting light comprises a bundle of optical fibers and the optical viewing means includes a tube containing at least a portion of the optical fibers, and means for detachably engaging said tube with said inner envelope.

* * * * *